United States Patent
Mabrouk et al.

(10) Patent No.: US 9,474,794 B2
(45) Date of Patent: Oct. 25, 2016

(54) ANTIBODIES THAT BIND TO ADRENOMEDULLIN AND TO ADRENOMEDULLIN RECEPTORS AND THE USES THEREOF AS DRUGS

(75) Inventors: Kamel Mabrouk, Les Pennes Mirabeau (FR); L'Houcine Ouafik, Marseilles (FR); Carine Tesic, Marseilles (FR); Denis Bertin, Marseilles (FR); Caroline Berenguer-Daize, Marseilles (FR); Pierre-Marie Martin, Marseilles (FR)

(73) Assignees: Universite d'Aix-Marseille, Marseilles (FR); Centre National de la Recherche Scientifique, Paris (FR)

( * ) Notice: Subject to any disclaimer, the term of this patent is extended or adjusted under 35 U.S.C. 154(b) by 457 days.

(21) Appl. No.: 13/819,590

(22) PCT Filed: Aug. 30, 2011

(86) PCT No.: PCT/IB2011/053792
§ 371 (c)(1),
(2), (4) Date: Aug. 14, 2013

(87) PCT Pub. No.: WO2012/029023
PCT Pub. Date: Mar. 8, 2012

(65) Prior Publication Data
US 2013/0315912 A1    Nov. 28, 2013

(30) Foreign Application Priority Data
Aug. 30, 2010 (FR) .................................. 10 03472

(51) Int. Cl.
| | | |
|---|---|---|
| *A61K 39/395* | (2006.01) | |
| *C07K 16/00* | (2006.01) | |
| *A61K 39/00* | (2006.01) | |
| *C07K 14/575* | (2006.01) | |
| *C07K 14/705* | (2006.01) | |
| *C07K 14/72* | (2006.01) | |
| *C07K 16/26* | (2006.01) | |
| *C07K 16/28* | (2006.01) | |

(52) U.S. Cl.
CPC .......... *A61K 39/0011* (2013.01); *C07K 14/575* (2013.01); *C07K 14/705* (2013.01); *C07K 14/72* (2013.01); *C07K 16/26* (2013.01); *C07K 16/2869* (2013.01); *A61K 2039/505* (2013.01); *A61K 2039/507* (2013.01); *C07K 2317/76* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,101,548 B2 * | 9/2006 | Cuttitta | C07K 14/575 424/130.1 |
| 9,028,818 B2 * | 5/2015 | Ouafik | C07K 16/28 424/130.1 |
| 2007/0004630 A1 | 1/2007 | Cuttitta et al. | |
| 2011/0293634 A1 | 12/2011 | Ouafik et al. | |

FOREIGN PATENT DOCUMENTS

| | | |
|---|---|---|
| WO | 02/066492 | 8/2002 |
| WO | 2007/045927 | 4/2007 |
| WO | 2010/012911 | 2/2010 |

OTHER PUBLICATIONS

Kaafarani et al. 2009. FASEB J. 23:3424-3435, e-published Jun. 22, 2009.*
Qi, Structure-Function Relationships of the N-Terminus of Receptor Activity-Modifying Proteins, British Journal of Pharmacology, 159, pp. 1059-1068, 2010.

* cited by examiner

*Primary Examiner* — Shulamith H Shafer
(74) *Attorney, Agent, or Firm* — Morgan, Lewis & Bockius LLP

(57) ABSTRACT

The invention relates to antibodies that bind to adrenomedullin and to proteins forming adrenomedullin receptors and to the uses thereof as drugs.

16 Claims, 10 Drawing Sheets

Figure 1:
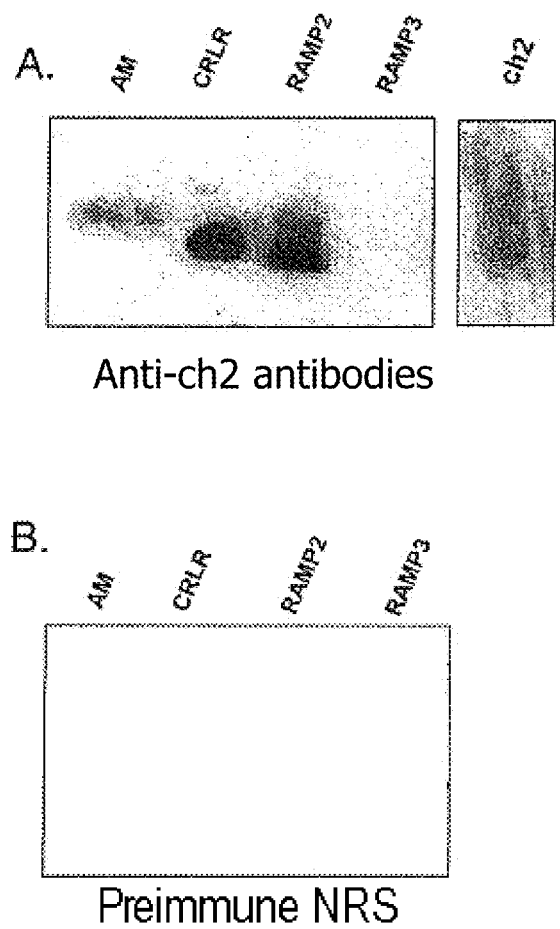

SEQUENCE LISTING

```
<160> NUMBER OF SEQ ID NOS: 10

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 24
<212> TYPE: PRT
<213> ORGANISM: Artificial
<220> FEATURE:
<223> OTHER INFORMATION: Peptide dirivi de l'adrinomidulline

<400> SEQUENCE: 2
```

```
Arg Ser Phe Arg Phe Gly Lys Leu Ala Thr Asp Lys Asp Lys Asp Asn
1               5                   10                  15

Val Ala Pro Arg Ser Lys Ile Ser
            20

<210> SEQ ID NO 3
<211> LENGTH: 25
<212> TYPE: PRT
<213> ORGANISM: Artificial
<220> FEATURE:
<223> OTHER INFORMATION: Peptide dirivi de hCLR

<400> SEQUENCE: 3

Ser Pro Glu Asp Ser Ile Gln Leu Gly Val Thr Arg Asn Lys Ile Met
1               5                   10                  15

Thr Ala Gln Tyr Glu Ala Tyr Gln Lys
            20                  25

<210> SEQ ID NO 4
<211> LENGTH: 31
<212> TYPE: PRT
<213> ORGANISM: Artificial
<220> FEATURE:
<223> OTHER INFORMATION: Peptide dirivi de hCLR

<400> SEQUENCE: 4

Pro Asp Tyr Phe Gln Asp Phe Asp Pro Ser Glu Lys Val Thr Lys Ile
1               5                   10                  15

Ala Asp Gln Asp Gly Asn Trp Phe Arg His Pro Ala Ser Asn Arg
            20                  25                  30

<210> SEQ ID NO 5
<211> LENGTH: 23
<212> TYPE: PRT
<213> ORGANISM: Artificial
<220> FEATURE:
<223> OTHER INFORMATION: Peptide dirivi de hRAMP2

<400> SEQUENCE: 5

Lys Asn Tyr Glu Thr Ala Val Gln Phe Ala Trp Asn His Tyr Lys Asp
1               5                   10                  15

Gln Met Asp Pro Ile Glu Lys
            20

<210> SEQ ID NO 6
<211> LENGTH: 28
<212> TYPE: PRT
<213> ORGANISM: Artificial
<220> FEATURE:
<223> OTHER INFORMATION: Peptide dirivi de hRAMP2

<400> SEQUENCE: 6

Arg Pro Tyr Ser Thr Leu Arg Asp Ala Leu Glu His Phe Ala Glu Leu
1               5                   10                  15

Phe Asp Leu Gly Phe Pro Asn Pro Leu Ala Glu Arg
            20                  25

<210> SEQ ID NO 7
<211> LENGTH: 6
<212> TYPE: PRT
<213> ORGANISM: Artificial
<220> FEATURE:
<223> OTHER INFORMATION: Peptide dirivi de hRAMP3
```

```
<400> SEQUENCE: 7

Lys Val Asp Val Trp Lys
1               5

<210> SEQ ID NO 8
<211> LENGTH: 22
<212> TYPE: PRT
<213> ORGANISM: Artificial
<220> FEATURE:
<223> OTHER INFORMATION: Peptide dirivi de hRAMP3

<400> SEQUENCE: 8

Leu Glu Arg Leu Pro Leu Ala Gly Lys Ala Phe Ala Asp Met Met Gly
1               5                   10                  15

Lys Val Asp Val Trp Lys
            20

<210> SEQ ID NO 9
<211> LENGTH: 22
<212> TYPE: PRT
<213> ORGANISM: Artificial
<220> FEATURE:
<223> OTHER INFORMATION: Peptide dirivi de hRAMP3

<400> SEQUENCE: 9

Gly Phe Ile Thr Gly Ile His Arg Gln Phe Phe Ser Asn Ala Thr Val
1               5                   10                  15

Asp Arg Val His Leu Glu
            20

<210> SEQ ID NO 10
<211> LENGTH: 78
<212> TYPE: PRT
<213> ORGANISM: Artificial
<220> FEATURE:
<223> OTHER INFORMATION: Polypeptide chimhre

<400> SEQUENCE: 10

Arg Ser Phe Arg Phe Gly Lys Leu Ala Thr Asp Lys Asp Lys Asp Asn
1               5                   10                  15

Val Ala Pro Arg Ser Lys Ile Ser Pro Asp Tyr Phe Gln Asp Phe Asp
            20                  25                  30

Pro Ser Glu Lys Val Thr Lys Ile Ala Asp Gln Asp Gly Asn Trp Phe
        35                  40                  45

Arg Lys Val Asp Val Trp Lys Lys Asn Tyr Glu Thr Ala Val Gln Phe
    50                  55                  60

Ala Trp Asn His Tyr Lys Asp Gln Met Asp Pro Ile Glu Lys
65                  70                  75
```

ANTIBODIES THAT BIND TO ADRENOMEDULLIN AND TO ADRENOMEDULLIN RECEPTORS AND THE USES THEREOF AS DRUGS

SEQUENCE LISTING SUBMISSION VIA EFS-WEB

A computer readable text file, entitled "045636-5222_SequenceListing.txt," created on or about Feb. 27, 2013, with a file size of about 5 kb contains the sequence listing for this application and is hereby incorporated by reference in its entirety.

The present invention relates to the field of antibodies directed against adrenomedullin receptors and used as medicaments, intended in particular for treating cancers.

Adrenomedullin (AM) is a vasoactive peptide of 52 amino acids (represented as sequence SEQ ID No. 1) which acts locally as an autocrine/paracrine hormone and exerts multiple biological actions (Hinson et al., *Endocr Rev.*, 2000, 21:138-67; Caron and Smithies, *Proc Natl Acad Sci USA*, 2001, 98:615-619; Shindo et al., *Circulation*, 2001, 104:1964-1971). Adrenomedullin receptors are present not only in the cells of most tissues, such as the heart, the kidney, the brain, the lung and the adrenal gland, but also in tumor stromal cells.

Adrenomedullin plays a positive role in the regulation of angiogenesis during vascular remodeling in response to ischemia, in the female reproductive system during embryonic vascular development, and during the development and vascularization of the placenta. Several teams have demonstrated a role for this peptide in the proliferation, migration and invasion of endothelial cells (Ouafik et al., *Am J Pathol.*, 2002, 160:1279-92; Kim et al., Faseb J., 2003, 17:1937-9; Fernandez-Sauze et al., *Int J Cancer*, 2004, 108:797-804). It has also been shown that adrenomedullin acts on one of the final steps of neovascularization which consists of the reorganization of endothelial cells into tubules, independently of VEGF (Fernandez-Sauze et al., 2004, mentioned above).

A role for adrenomedullin in tumor growth has, moreover, been demonstrated (Ouafik et al., *Am J Pathol.*, 2002, 160:1279-92; Martinez et al., *J Natl Cancer Inst.*, 2002, 94:1226-37; Oehler et al., *Oncogene*, 2001, 20:2937-45; Ishikawa et al., *Oncogene*, 2003, 22:1238-1242). Several studies demonstrate that adrenomedullin has angiogenic properties in most tumors (breast, prostate, colon, lung, kidney, respiratory tracts, bladder) (Ouafik et al., 2002, mentioned above; Fernandez-Sauze et al., 2004, mentioned above; Nikitenko et al., *Br J Cancer*, 2006, 94:1-7). For example, in adrenomedullin+/−heterozygous mice, the tumor volume decreases compared with wild-type mice (Iimuro et al., *Circ. Res.*, 2004, 95:415-423). This effect is associated with a reduction in neovascularization. Blocking the action of adrenomedullin with an antagonist (adrenomedullin$_{22-52}$) inhibits the growth of xenografted pancreatic tumors by destabilizing tumor vascularization (Ishikawa et al., *Oncogene*, 2003, 22:1238-1242). Similar effects have been observed in xenografts grown from glial tumor cells (Ouafik et al., 2002, mentioned above).

Adrenomedullin receptors (AMRs) are multiprotein complexes composed of the association of at least two proteins, CRLR (calcitonin receptor like receptor) and a RAMP protein (receptor activity-modifying protein) (McLatchie et al., *Nature*, 1998, 6683:333-9).

The CLR receptor (CRLR) was isolated in 1993 (Njuki et al., *Clin Sci.*, 1993, 4:385-8; Chang et al., *Neuron.*, 1993, 6:1187-95). It comprises seven G-protein-coupled transmembrane domains. The CLR peptide sequence was established in humans in 1996 (Aiyar et al., *J Biol Chem.*, 1996, 19:11325-9) and in pigs in 1998 (Elshourbagy et al., *Endocrinology*, 1998, 4:1678-83). The CLR belongs to class II of the GPCRs (G-protein-coupled receptors), a class which groups together receptors for peptides such as glucagon and glucagon-like peptides (GLPs), secretin, parathormone or calcitonin. GPCRs are of polypeptide nature and comprise an extracellular portion bearing the ligand-binding site, a seven-helix transmembrane portion and an intracellular portion in contact with the G proteins which perform the transfer and amplification of the signal received by the receptor. GPCRs have three extracellular loops (called E1, E2 and E3) and three intracellular loops (I1, I2 and I3) (Bockaert and Pin, *Embo J.*, 1999, 18:1723-1729). These proteins can be subject to post-translational modifications, such as N-glycosylation, or acetylation by lipid compounds sometimes forming a fourth intracellular pseudo-loop (I4) (Assie et al., *EMC-Endocrinologie*, 2004, 1:169-199).

In 1998, McLatchie and collaborators (reference mentioned above) demonstrated that the CLR receptor can generate two pharmacologically distinct receptors by association with a family of proteins, of 160 amino acids (14-21 kDa), comprising a single transmembrane domain, called RAMPs. The CLR is correctly functional only in the state of a dimer with a RAMP protein.

Three RAMP protein isoforms exist: RAMP1, 2 and 3. These proteins have less than 30% identity with one another, but exhibit structural organization similarities. In humans, the genes encoding RAMP1, RAMP2 and RAMP3 are carried respectively by chromosomes 2, 17 and 7. The RAMP proteins consist of a single transmembrane domain; the extracellular N-terminal end is relatively long and plays an important role in the specialization and the functionality of the receptor (CGRP or adrenomedullin) (Kuwasako et al., *J Biol Chem.*, 2001, 275:29602-9).

Two essential functions are attributed to RAMP proteins:
receptor determination: the fundamental role of RAMP proteins is to define the specificity of the ligand that interacts directly at the cell surface. RAMP1 exhibits the CLR as a mature glycoprotein so as to form the CGRP (calcitonin gene-related peptide) receptor. Likewise, RAMP2 and RAMP3 exhibit the CLR as a mature glycoprotein so as to form adrenomedullin receptors. Thus, the nature of the RAMP proteins present in a cell type, the protein interactions that are established between the various partners (CLR, RAMP1, RAMP2, RAMP3) and the proportion of each of the proteins allow cells to respond specifically to various neuropeptides (Bühlmann et al., *FEBS Lett.*, 2000, 486:320-4; Chakravarty et al., *Br J Pharmacol.*, 2000, 130:189-95);

intracellular transport: the CLR requires the coexpression of RAMP proteins for its transport to the cytoplasmic membrane (Sexton et al., *Cell Signal*, 2001, 13:73-83). The converse is true: RAMP proteins need the CLR for their translocation to the cell surface (Flahaut et al., *J Biol Chem.*, 2002, 277:14731-7).

Some of the inventors have already shown (International application WO 2010/012911) that a mixture of at least three antibodies which bind to three different proteins forming the adrenomedullin receptors, more particularly the hCLR, hRAMP2 and hRAMP3 proteins, exhibit a significantly greater antitumor efficacy in vitro and in vivo compared with the use of a single anti-CLR, anti-RAMP2 or anti-RAMP3 antibody, or even compared with the use of a mixture of two anti-CLR/anti-RAMP2 or anti-CLR/anti-RAMP3 antibodies.

However, there is still a need to improve the treatments for diseases in which angiogenesis must be inhibited, especially cancer. In particular, there is a real need to have new antibodies (serotherapy) or antigens (immunotherapy) for combating these diseases more effectively.

The inventors have now synthesized a chimeric polypeptide (also known as antigen) consisting of 4 peptide sequences derived, respectively, from adrenomedullin and from the human adrenomedullin receptors hRCLR, hRAMP2 and hRAMP3. They obtained, in rabbits, polyclonal antibodies directed against this chimeric polypeptide, which bind to adrenomedullin, hCLR, hRAMP2 and hRAMP3. They then showed that these polyclonal antibodies, which are adrenomedullin, hCLR, hRAMP2 and hRAMP3 antagonists, exhibited an antitumor efficacy in vitro. They also showed, in vivo in mice, that the intraperitoneal administration of these anti-chimeric polypeptide antibodies, on the one hand, induces an inhibition of glioblastoma (U87) tumor growth by 70% to 75% after 11 days and up to 31 days of treatment, and, on the other hand, inhibits the recruitment of vascular cells (endothelial cells and pericytes). More particularly, the results obtained in the in vivo angiogenesis test demonstrate the capacity of these anti-chimeric polypeptide antibodies to inhibit the recruitment of vascular cells from the first dose used, of 25 µg/mouse, whereas the equivalent of this inhibition with a mixture of three antibodies which bind to the hCLR, hRAMP2 and hRAMP3 proteins is observed only with a dose of 300 µg/mouse, and the inhibition remains partial with an anti-adrenomedullin antibody at a dose of 500 µg/mouse.

It also emerges from these results that such a chimeric polypeptide (antigen) can be used for preparing a vaccine intended for the treatment of a disease in which angiogenesis must be inhibited.

A subject of the present invention is therefore a mixture of at least 4 antibodies and/or fragments of said antibodies which bind respectively to adrenomedullin and to the CLR, RAMP2 and RAMP3 proteins, said antibodies and/or fragments of said antibodies being antagonists of adrenomedullin and of the CLR, RAMP2 and RAMP3 proteins.

A subject of the present invention is also said mixture of antibodies and/or fragments of said antibodies for use as a medicament or for the preventive or curative treatment of a disease in which angiogenesis must be inhibited, preferably chosen from cancer, inflammatory diseases, psoriasis, atherosclerosis and macular degeneration, more preferably cancer.

Advantageously, said medicament is intended for the preventive or curative treatment of tumors, preferentially those in which vascularization is necessary for their growth, more particularly solid tumors.

According to one preferred embodiment of the present invention, the adrenomedullin and said CLR, RAMP2 and RAMP3 proteins are those of a mammal, and more preferably are of human origin. The amino acid sequences of the CLR, RAMP2 and RAMP3 proteins of human origin are well known and are respectively available under accession numbers gi|5031621, gi|118572585 and gi|5032023 in the Genbank database.

According to one advantageous embodiment of the present invention, said antibodies and antibody fragments bind to an extracellular domain of the CLR, RAMP2 and RAMP3 proteins, and more particularly to the peptides of sequences SEQ ID No. 3 or 4 for the anti-CLR antibodies, to the peptides of sequences SEQ ID No. 5 or 6 for the anti-RAMP2 antibodies and to the peptides of sequences SEQ ID No. 7, 8 or 9 for the anti-RAMP3 antibodies.

The invention encompasses the natural, recombinant or synthetic polyclonal or monoclonal antibodies, the chimeric antibodies, such as humanized antibodies, and also the fragments thereof (for example: Fab'2, Fab, Fv, scFv, VHH) which have retained their ability to bind to adrenomedullin, CLR, RAMP2 or RAMP3.

The term "recombinant antibody" is intended to mean an antibody produced by genetic engineering, for example by cloning and gene amplification.

The term "synthetic antibody" is intended to mean an antibody produced by enzymatic and/or chemical synthesis.

The term "chimeric antibody" is intended to mean an antibody of a particular animal species or of a particular class of antibody, which comprises all or part of a heavy chain and/or of a light chain of an antibody of another animal species or of another antibody class. The term "chimeric antibody" can also denote a multispecific antibody, i.e. an antibody which is specific for at least two different epitopes. The multispecific antibody can be obtained from said antibody fragments as defined above. In other words, the mixture of antibody fragments as defined above can be in the form of one or more multispecific antibody or antibodies.

Advantageously, said multispecific antibody binds to two or three different epitopes chosen from an adrenomedullin epitope, a CLR epitope, a RAMP2 epitope and a RAMP3 epitope. By way of example of a bispecific antibody, mention may be made of an antibody which binds to a complex chosen from AM/CLR, AM/RAMP2, AM/RAMP3, CLR/RAMP2, CLR/RAMP3 and RAMP2/RAMP3, preferably a complex chosen from CLR/RAMP2, CLR/RAMP3 and RAMP2/RAMP3. By way of example of a trispecific antibody, mention may be made of an antibody which binds to a complex chosen from AM/CLR/RAMP2, AM/CLR/RAMP3, AM/RAMP2/RAMP3 and CLR/RAMP2/RAMP3, preferably the CLR/RAMP2/RAMP3 complex.

Advantageously still, said multispecific antibody binds to adrenomedullin and to the CLR, RAMP2 and RAMP3 proteins.

The term "humanized antibody" is intended to mean a human immunoglobulin in which the residues of the CDRs (complementarity-determining regions) which form the antigen-binding site are replaced with those of a nonhuman monoclonal antibody having the desired specificity, affinity or activity. In comparison with nonhuman antibodies, humanized antibodies are less immunogenic and have an extended half-life in humans since they have only a low proportion of nonhuman sequences given that virtually all the residues of the FR (framework) regions and of the constant region (Fc) of these antibodies are those of a human immunoglobulin consensus sequence.

Preferred antibodies are monoclonal antibodies and humanized antibodies.

The antibodies according to the invention and the fragments thereof are prepared by the conventional techniques known to those skilled in the art.

The binding of an antibody or of an antibody fragment according to the present invention to adrenomedullin, CLR, RAMP2 and RAMP3 can be determined by carrying out an appropriate immunological method, for example by ELISA, RIA, immunofluorescence or immunohistochemistry.

Said anti-CLR, -RAMP2 and -RAMP3 antibodies or antibody fragments are adrenomedullin receptor antagonists, i.e. they block (or inhibit), in a dose-dependent manner, the binding of adrenomedullin to these receptors (CLR, RAMP2 and RAMP3).

Said anti-adrenomedullin antibodies or antibody fragments also block (or inhibit), in a dose-dependent manner, the binding of adrenomedullin to these receptors.

The production of anti-AM, -CLR, -RAMP2 or -RAMP3 antibodies is known to those skilled in the art. It is described, for example, in Ouafik et al. (*Am J Pathol.*, 2002, 160:1279-92), Fernandez-Sauze et al. (*Int J Cancer*, 2004, 108:797-804) and International applications WO 2007/045927 and WO 2010/012911.

Advantageously, the antibodies according to the present invention can be obtained by immunization of an animal with a chimeric polypeptide (antigen) comprising or consisting of four peptides of at least 6 contiguous amino acids derived, respectively, from adrenomedullin and from an extracellular domain of the CLR, RAMP2 and RAMP3 proteins, said chimeric polypeptide being capable of inducing, in said animal immunized with said chimeric polypeptide, the production of polyclonal antibodies which bind to adrenomedullin, CLR, RAMP2 and RAMP3.

Preferably, the animal immunized is a mammal, such as, for example, the horse, the goat, the rabbit, the rat, the mouse, the llama and the camel, and more preferably the rabbit or the mouse.

More specifically:
the polyclonal antibodies are prepared by immunization of an appropriate animal with an antigen (chimeric polypeptide) as defined above, optionally coupled to KLH or to albumin and/or combined with an appropriate adjuvant, such as Freund's adjuvant (complete or incomplete) or alumina hydroxide; after a satisfactory antibody titer has been obtained, the antibodies are harvested by taking a serum sample from the immunized animals and enriched with IgG by precipitation, according to the conventional techniques, and then the IgGs specific for adrenomedullin and for the CLR, RAMP2 and RAMP3 proteins are optionally purified by affinity chromatography on an appropriate column to which said protein or the antigen as defined above is attached, so as to obtain a preparation of monospecific IgGs;

the monoclonal antibodies are produced from hybridomas obtained by fusion of B lymphocytes of an animal immunized with the antigen as defined above, with myelomas, according to the techniques well known to those skilled in the art; the hybridomas are cultured in vitro, in particular in fermenters, or produced in vivo, in the form of ascites; alternatively, said monoclonal antibodies are produced by genetic engineering;

the humanized antibodies are produced by general methods also well known to those skilled in the art;

the antibody fragments are produced from the $V_H$ and $V_L$ regions which have been cloned, from the mRNAs of hybridomas or of splenic lymphocytes from an immunized animal (e.g. a mouse or a member of the camel family); for example, the Fv, scFv, Fab and VHH (or nanobody, obtained by immunizing a member of the camel family) fragments are expressed at the surface of filamentous phages according to techniques well known to those skilled in the art; after several selection steps, the antigen-specific antibody fragments are isolated and expressed in an appropriate expression system, by conventional cloning and recombinant DNA expression techniques.

The antibodies or the fragments thereof as defined above are purified by conventional techniques known to those skilled in the art, such as affinity chromatography.

The expression "peptide of at least 6 contiguous amino acids which is derived from adrenomedullin or from the CLR, RAMP2 or RAMP3 adrenomedullin receptors" is intended to mean a fragment of at least 6 contiguous amino acids of adrenomedullin or of said adrenomedullin receptors, or a fragment of at least 6 contiguous amino acids of adrenomedullin or of said adrenomedullin receptors in which one or more amino acid residues has (have) been deleted, and/or one or more amino acid residues has (have) been substituted with a natural or unnatural amino acid residue or an amino acid residue with a configuration of D or beta type, and/or one or more natural or unnatural amino acid residues has (have) been inserted therein, and/or one or more amide bonds has (have) been modified, it being understood that said peptide derived from adrenomedullin or from said adrenomedullin receptors comprises or consists of at least 6 contiguous amino acids of adrenomedullin or of said adrenomedullin receptors.

Advantageously, said peptides consist of 20 to 35 amino acids.

A chimeric polypeptide (antigen) as defined above, which mimics the structure of the extracellular domains of the CLR, RAMP2 and RAMP3 proteins, can induce the production, in immunized individuals, of conformational antagonist antibodies which specifically recognize these CLR, RAMP2 and RAMP3 proteins in their native form or protein complexes, i.e. the AM/CLR, AM/RAMP2, AM/RAMP3, CLR/RAMP2, CLR/RAMP3, RAMP2/RAMP3, AM/CLR/RAMP2, AM/CLR/RAMP3, AM/RAMP2/RAMP3, CLR/RAMP2/RAMP3 or AM/CLR/RAMP2/RAMP3 complexes.

More advantageously, each of the following peptides can be used to obtain a chimeric polypeptide according to the present invention:
peptide derived from adrenomedullin, consisting of the concatenation of the R12-F14, R17-G19, K25-A27 and T34-S48 fragments of adrenomedullin:

(SEQ ID No. 2)
RSFRFGKLATDKDKDNVAPRSKIS, peptides derived from the S27-K51 (SEQ ID No. 3) or P89-R119 (SEQ ID No. 4) fragments of the hCLR protein:

(SEQ ID No. 3)
SPEDSIQLGVTRNKIMTAQYEAYQK, (SEQ ID No. 4)
PDYFQDFDPSEKVTKIADQDGNWFRHPASNR, peptides derived from the K59-K81 (SEQ ID No. 5) or R91-R118 (SEQ ID No. 6) fragments of the hRAMP2 protein:

(SEQ ID No. 5)
KNYETAVQFAWNHYKDQMDPIEK, (SEQ ID No. 6)
RPYSTLRDALEHFAELFDLGFPNPLAER, peptides derived from the K49-K55 (SEQ ID No. 7), L34-K55 (SEQ ID No. 8) or G91-E112 (SEQ ID No. 9) fragments of the hRAMP3 protein:

```
KVDVWK,                                          (SEQ ID No. 7)

LERLPLAGKAFADMMGKVDVWK,                          (SEQ ID No. 8)

GFITGIHRQFFSNATVDRVHLE.                          (SEQ ID No. 9)
```

The amino acid residue denoted "A" corresponds to an alanine residue obtained by substitution of a cysteine residue present in the peptide sequence of the natural hCLR, hRAMP2 or hRAMP3 proteins. Substituting the cysteine residue with an alanine makes it possible to obtain a well-characterized linear peptide sequence and avoids obtaining mixtures of peptides comprising dimmers (via the formation of interchain disulfide bridges).

The order of the various peptides derived, respectively, from adrenomedullin and from the CLR, RAMP2 and RAMP3 adrenomedullin receptors in the chimeric polypeptide according to the present invention can be random. However, a chimeric polypeptide comprising or consisting of, from its N-terminal end to its C-terminal end, a peptide derived from adrenomedullin, a peptide derived from CLR, a peptide derived from RAMP3 and a peptide derived from RAMP2, as defined above, will be preferred.

According to one preferred embodiment of the present invention, said chimeric polypeptide (antigen) has the sequence SEQ ID No. 10 (referred to as ch2):

```
RSFRFGKLATDKDKDNVAPRSKISPDYFQDFDPSEKVTKIADQDGNWFR
KVDVWKKNYETAVQFAWNHYKDQMDPIEK.
```

The invention also encompasses the chimeric polypeptides (antigens) made up of sequences that are functionally equivalent to the sequences as defined above, i.e. capable of inducing the production, in the immunized individuals, of antagonist antibodies which specifically recognize adrenomedullin and the CLR, RAMP2 and RAMP3 adrenomedullin receptors. Among these sequences, mention may, for example, be made of the sequences derived from the preceding sequences by:
  substitution and/or elimination and/or addition of one or
    more amino acids of the sequences as defined above,
  modification of at least one —CO—NH— peptide bond
    of the peptide chain of the antigen as defined above, in
    particular by replacement with a bond different than the
    —CO—NH— bond (e.g. methyleneamino, carba,
    ketomethylene, thioamide) or by introduction of a bond
    of retro or retro-inverso type, and/or
  substitution of at least one amino acid of the peptide chain
    of the antigen as defined above, with a non-proteinogenic amino acid residue.

The term "non-proteinogenic amino acid residue" is intended to mean any amino acid which does not go to make up a natural protein or peptide, in particular any amino acid of which the carbon bearing the side chain R, namely the —CHR— group, located between —CO— and —NH— in the natural peptide chain, is replaced with a motif which does not go to make up a natural protein or peptide.

A subject of the present invention is also a method for obtaining polyclonal antibodies which bind to adrenomedullin or to the CLR, RAMP2 or RAMP3 proteins, comprising a step of immunizing an animal as defined above with a chimeric polypeptide (antigen) as defined above, preferably the chimeric polypeptide of sequence SEQ ID No. 10.

A subject of the present invention is also a pharmaceutical composition comprising at least one mixture of antibodies and/or fragments of said antibodies, as defined above, and at least one pharmaceutically acceptable vehicle.

By way of nonlimiting examples of a pharmaceutically acceptable vehicle, mention may be made of dispersants, solubilizing agents, stabilizers, preservatives, etc. Pharmaceutically acceptable vehicles that can be used in formulations (liquid and/or injectable and/or solid formulations) are in particular methylcellulose, hydroxymethylcellulose, carboxymethylcellulose, cyclodextrins, polysorbate 80, mannitol, gelatin, lactose, vegetable or animal oils, acacia, etc.

Said medicament or said pharmaceutical composition can be in the form of an isotonic and buffered, physiological saline solution compatible with pharmaceutical use and known to those skilled in the art.

Said medicament or said pharmaceutical composition can be formulated in any pharmaceutically acceptable form, for instance in the form of an injectable suspension, of gels, oils, tablets, suppositories, gel capsules, capsules, etc., optionally used by means of galenic forms or devices which provide prolonged and/or delayed release. For this type of formulation, use is advantageously made of an agent such as cellulose, carbonates or starches.

It is possible for the mixture of antibodies and/or antibody fragments according to the present invention to comprise both polyclonal antibodies and monoclonal antibodies as defined above.

In said mixture, said antibodies and/or antibody fragments can be present in any ratio with respect to one another, for instance a ratio of between 0.1 and 10. A preferential ratio is a ratio of 1.

The amount of antibodies or of antibody fragments used as medicament according to the invention or present in the pharmaceutical composition according to the invention can be modulated so as to obtain a circulating level of active ingredient (in a physiological fluid such as blood) required to obtain the desired therapeutic effect for a particular subject. The amount chosen will depend on many factors, in particular on the route of administration, the duration of administration, the moment at which the administration is carried out, the rate of elimination of the compound, the various product(s) used in combination with said medicament or said pharmaceutical composition, the age, the weight and the physical condition of the patient, and also the medical history thereof, and any other information known in medicine.

The prescription by the treating physician may begin at doses lower than those generally used for antibodies, and these doses will gradually be increased in order to have better control over the appearance of any side effects.

Generally, the daily dose of the compound will be the minimum dose for obtaining the therapeutic effect. This dose will depend on the various factors mentioned previously. The doses will generally be between 0.1 and 100 mg per kg per day for human beings, and preferentially between 4 and 25 mg per kg and per day and even more advantageously between 7 and 14 mg per kg and per day.

If necessary, the daily dose can be administered in two, three, four, five, six or more intakes per day or via multiple subdoses administered at appropriate intervals during the day.

Advantageously, the composition according to the present invention is preferably administered parenterally or directly, if this is possible, into the tumor (intratumor administration).

The medicament or the pharmaceutical composition according to the present invention can be used alone or in combination with at least one other therapeutically active compound, such as, for example, an anticancer compound. The use of said medicament or of said pharmaceutical composition, and of said therapeutically active compound, can be simultaneous, separate or spread out over time, in particular during a treatment of a subject suffering from cancer.

A subject of the present invention is also a chimeric polypeptide (antigen) as defined above, preferably the polypeptide of sequence SEQ ID No. 10, for use as a medicament, preferably as a vaccine, more preferably as a vaccine intended for the preventive or curative treatment of a disease in which angiogenesis must be inhibited, such as cancer, inflammatory diseases, psoriasis, atherosclerosis and macular degeneration, preferably cancer.

Advantageously, said vaccine is intended for the preventive or curative treatment of tumors, preferentially those in which vascularization is necessary for their growth, more particularly solid tumors.

The antigens according to the invention are prepared by the conventional solid-phase or liquid-phase synthesis techniques, known per se to those skilled in the art.

Alternatively, they can be prepared by recombinant DNA techniques, also known per se to those skilled in the art.

Consequently, a subject of the present invention is also an isolated nucleic acid molecule comprising a sequence encoding an antigen (chimeric polypeptide) as defined above.

The nucleic acid molecules according to the invention are obtained by conventional methods, known per se to those skilled in the art, according to standard protocols.

A subject of the present invention is also a eukaryotic or prokaryotic recombinant vector comprising an insert made up of a nucleic acid molecule encoding an antigen (chimeric polypeptide) as defined above. Many vectors into which it is possible to insert a nucleic acid molecule of interest in order to introduce it into and to maintain it in a eukaryotic or prokaryotic host cell are known per se; the choice of an appropriate vector depends on the use envisioned for this vector (for example, replication of the sequence of interest, expression of this sequence, maintaining of the sequence in extrachromosomal form or else integration into the chromosomal material of the host), and also on the nature of the host cell. For example, viral vectors or nonviral vectors such as plasmids can be used.

Preferably, said recombinant vector is an expression vector in which said nucleic acid molecule is placed under the control of appropriate transcription- and translation-regulating elements. In addition, said vector can comprise sequences (tags) fused in frame with the 5' and/or 3' end of said insert, which are of use for immobilizing and/or detecting and/or purifying the protein expressed from said vector.

These vectors are constructed and introduced into host cells by conventional recombinant DNA and genetic engineering methods which are known per se.

The subject of the present invention is also eukaryotic or prokaryotic cells modified with a recombinant vector as defined above.

The recombinant vectors and the transformed cells, as defined above, are of use in particular for producing the antigen as defined above.

A subject of the present invention is also an immunogenic composition, characterized in that it comprises an antigen (chimeric polypeptide) as defined above, optionally in the form of lipopeptide vesicles or micelles, combined with at least one pharmaceutically acceptable vehicle and optionally with at least one adjuvant.

The adjuvants used are adjuvants conventionally used in vaccine compositions, such as alumina hydroxide and squalene.

A subject of the present invention is also a method for treating or preventing, in a subject, a disease in which angiogenesis must be inhibited as defined above, comprising the administration, to said subject, of a therapeutically effective amount of said composition comprising a mixture of antibodies and/or fragments of said antibodies, as defined above, or of said immunogenic composition.

A subject of the present invention is also a method for obtaining monoclonal or polyclonal antibodies which bind to adrenomedullin, comprising a step of immunizing an animal as defined above with the polypeptide of sequence SEQ ID No. 2.

Figure 1C:
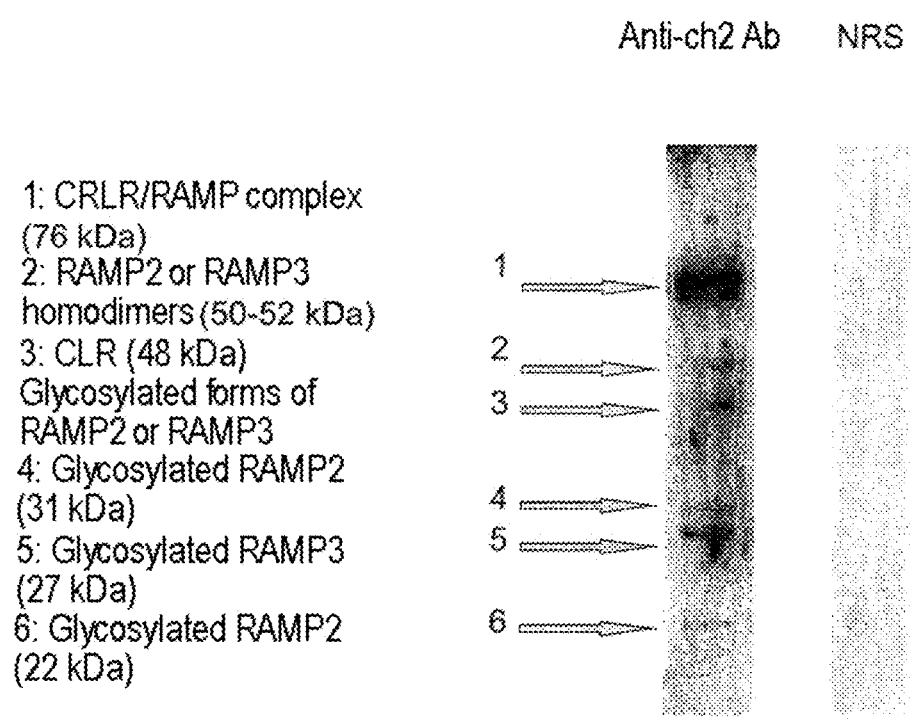

Other aspects and advantages of the present invention will become apparent on reading the examples which follow, which should be considered to be nonlimiting illustrations, and also the appended figures:

FIG. 1: demonstration of the specificity of the anti-AM-CLR-RAMP3-RAMP2 chimeric polypeptide polyclonal antibodies (anti-ch2 antibodies) by Western blotting. 750 ng of adrenomedullin (AM) and hRAMP3 peptide/protein, 500 ng of hCLR (referred to as CRLR) and hRAMP2 protein and 20 ng of AM-CLR-RAMP3-RAMP2 chimeric polypeptide (referred to as ch2) were separated by SDS-PAGE on a 17% acrylamide gel, and then visualized with the anti-AM-CLR-RAMP3-RAMP2 chimeric polypeptide polyclonal antibodies (FIG. 1A) or with the nonreactive serum (NRS) (FIG. 1B), used at 1/250. FIG. 1C represents the same experiment but carried out with 20 μg of protein extracts prepared from U87 glial tumor cells, separated by SDS-PAGE on a 12% acrylamide gel.

Figure 2:
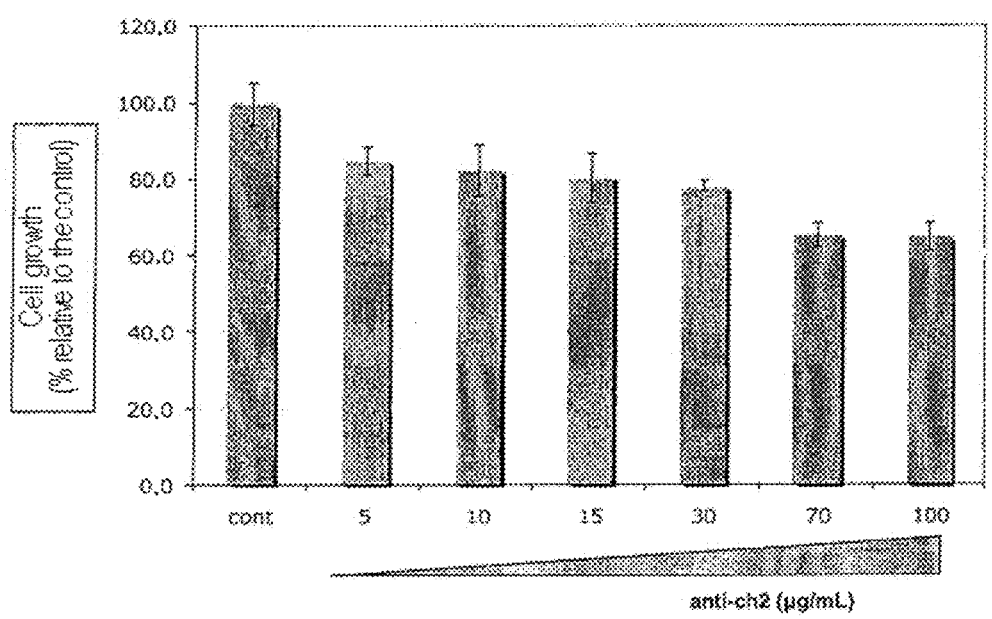

FIG. 2: effect of the anti-AM-CLR-RAMP3-RAMP2 chimeric polypeptide (anti-ch2) polyclonal antibodies on the growth of U87 glial tumor cells in vitro: 2000 cells per well were seeded into 24-well plates, and then treated for 6 days with the anti-AM-CLR-RAMP3-RAMP2 chimeric polypeptide antibodies or the preimmune serum (NRS) in 2%-serum medium (2% of fetal bovine serum in 100 ml of culture medium). An MTT ([3-(4,5-dimethylthiazol-2-yl)-2,5-diphenyltetrazolium bromide]) cell proliferation test was then used to evaluate the amount of cells at the end of the treatment.

Figure 3:
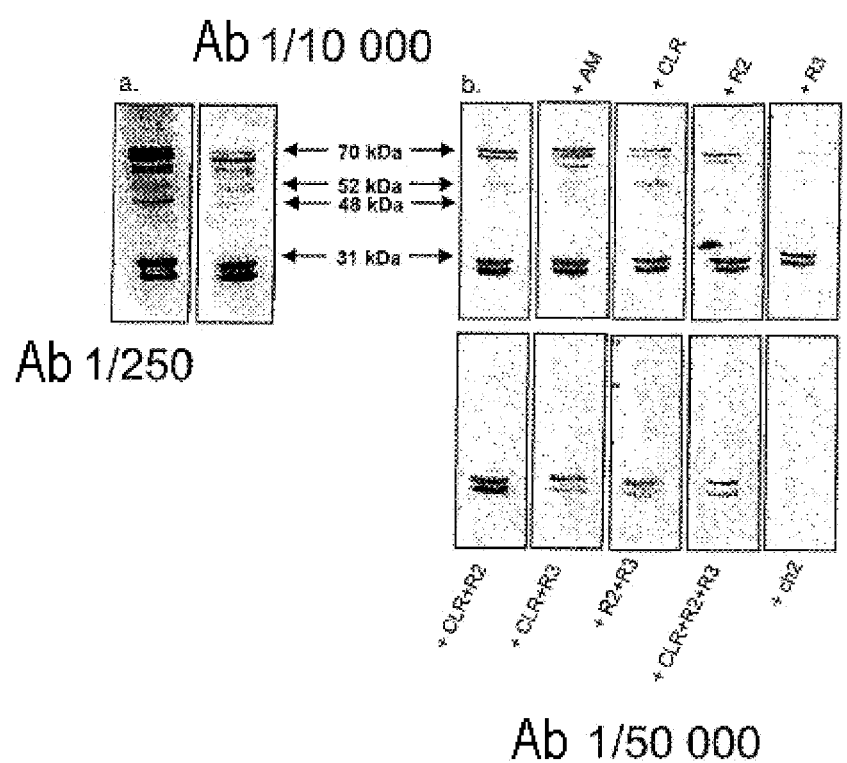

FIG. 3: Western blotting carried out using protein extracts of U87 glial tumor cells. 20 μg of total proteins were separated by SDS-PAGE on a 12% polyacrylamide gel and then visualized with the anti-AM-CLR-RAMP3-RAMP2 chimeric polypeptide polyclonal antibodies used at 1/250 or at 1/10 000 (FIG. 3A), or used at 1/50 000 (FIG. 3B) and preincubated for 30 min with 0.7 μg/ml of adrenomedullin (AM), hCLR (CLR), hRAMP2 (R2) or hRAMP3 (R3) or 1.4 μg/ml of hCLR/hRAMP2 (CLR+R2), hCLR/hRAMP3 (CLR+R3) or hRAMP2/hRAMP3 (R2+R3) protein complexes or 2.1 μg/ml of hCLR/hRAMP2/hRAMP3 (CLR+R2+R3) protein complex or 0.7 μg/ml of AM-CLR-RAMP3-RAMP2 chimeric polypeptide (ch2) (FIG. 3B). The band at 73 kDa corresponds to the hCLR/hRAMP2 or hCLR/hRAMP3 complex, the band at 50-52 kDa corresponds to the hRAMP2 or hRAMP3 homodimers, the band at 48 kDa corresponds to hCLR and the band at 31 kDa corresponds to glycosylated hRAMP2.

Figure 4:
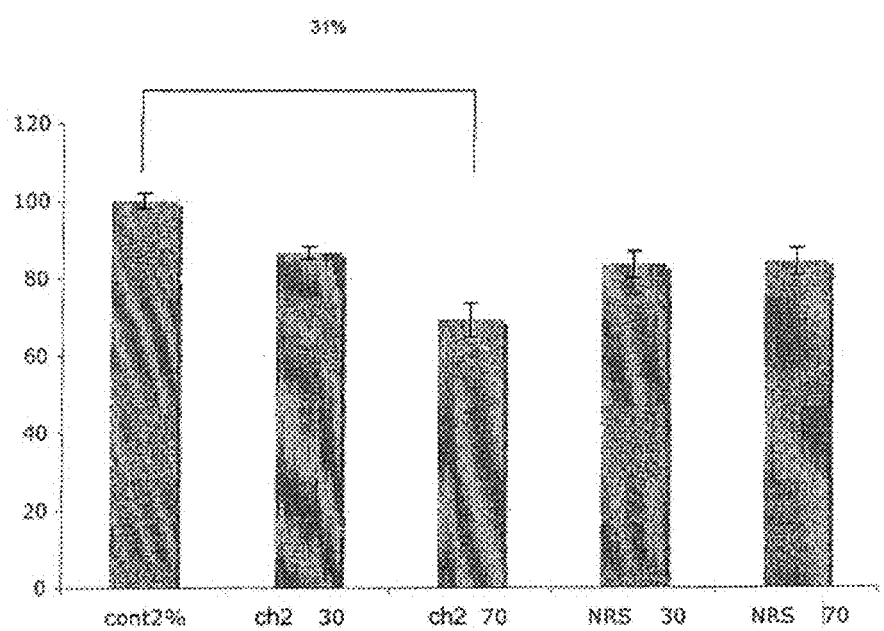

FIG. 4: in vitro effect of the anti-AM-CLR-RAMP3-RAMP2 chimeric polypeptide polyclonal antibodies on the growth of U87 cells. U87 glial tumor cells were seeded into 24-well plates (2000 cells/well) and treated for 6 days with the anti-AM-CLR-RAMP3-RAMP2 chimeric polypeptide polyclonal antibodies (referred to as ch2) at a concentration of 30 or 70 mg/ml or with the nonreactive serum (preimmune serum, NRS) at a concentration of 30 or 70 mg/ml or in 2%-serum medium (cont2%). An MTT test was then used to evaluate the amount of cells at the end of the treatment. The numbers "in FIG. 5: in vitro effect of the anti-AM-CLR-RAMP3-RAMP2 chimeric polypeptide polyclonal antibodies on the migration of U87 glial tumor cells. 20 000 U87 glial tumor cells were seeded into Boyden chambers in 2%-serum medium after having been pretreated (ch2) or not (contAM) with the anti-AM-CLR-RAMP3-RAMP2 chimeric polypeptide polyclonal antibodies or with the nonreactive serum (NRS), and were then subjected for 4 h to the chemoattractive effect of adrenomedullin ($10^{-7}$ M) located in the lower compartment of the Boyden chamber. A negative control was performed by omitting the adrenomedullin in the lower compartment of the Boyden chamber (cont). The evaluation of the number of cells having migrated was carried out by counting under a microscope after Dapi staining.

Figure 6:
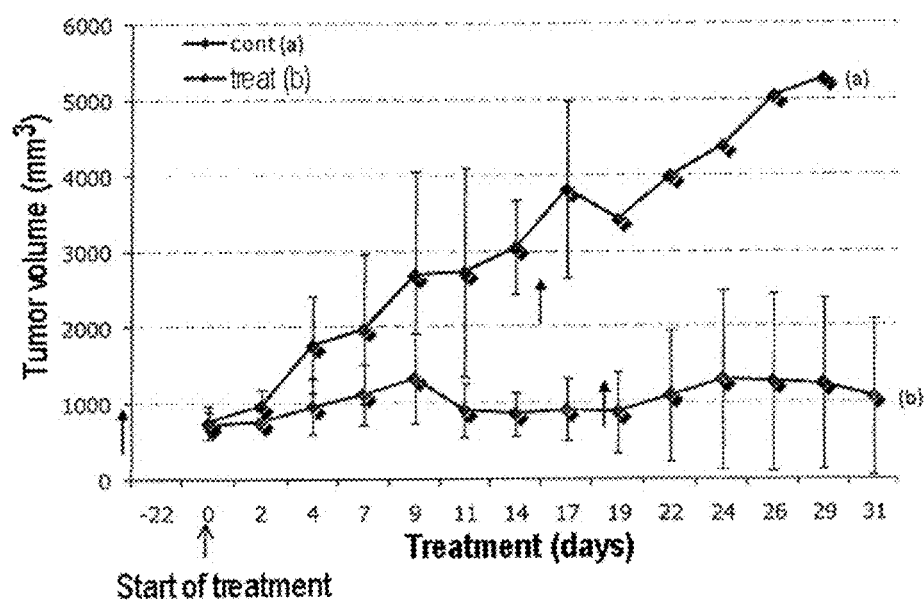

FIG. 6: graph showing the inhibition of tumor growth of U87 xenografts in mice after treatment with anti-AM-CLR-RAMP3-RAMP2 chimeric polypeptide antibodies. 2 million U87 cells were injected into mice subcutaneously. 24 days after the injection, the tumors reaching 600 to 800 mm$^3$, the mice were then separated into two groups: the control group receiving the preimmune serum NRS and the second group treated intraperitoneally with the anti-AM-CLR-RAMP3-RAMP2 chimeric polypeptide antibodies. After two weeks of treatment at a rate of 3 injections per week of 350 µg per injection of antibody, a 70% decrease in the tumor volume was observed.

Figure 7:
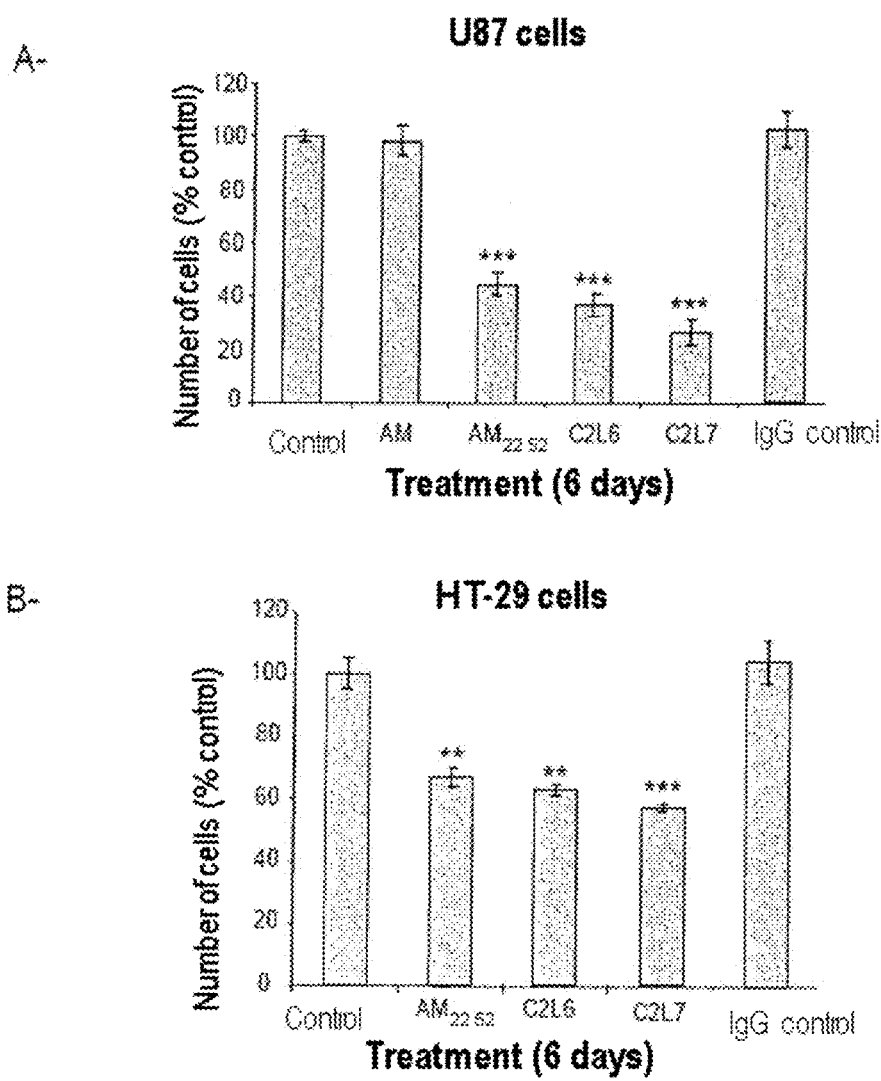

FIG. 7: in vitro effect of the anti-AM-CLR-RAMP3-RAMP2 chimeric polypeptide polyclonal antibodies on the proliferation of U87 glial tumor cells (A) and of HT-29 colorectal cancer cells (B). The cells were treated for 6 days with 2 different batches of anti-AM-CLR-RAMP3-RAMP2 chimeric polypeptide polyclonal antibodies (C2L6 and C2L7). The controls are: absence of treatment ("Control"); treatment with adrenomedullin ("AM"); treatment with the $AM_{22-52}$ antagonist ("$AM_{22-52}$"); treatment with IgGs not specific for AM, CLR, RAMP3 and RAMP2 ("IgG Control").

Figure 8:
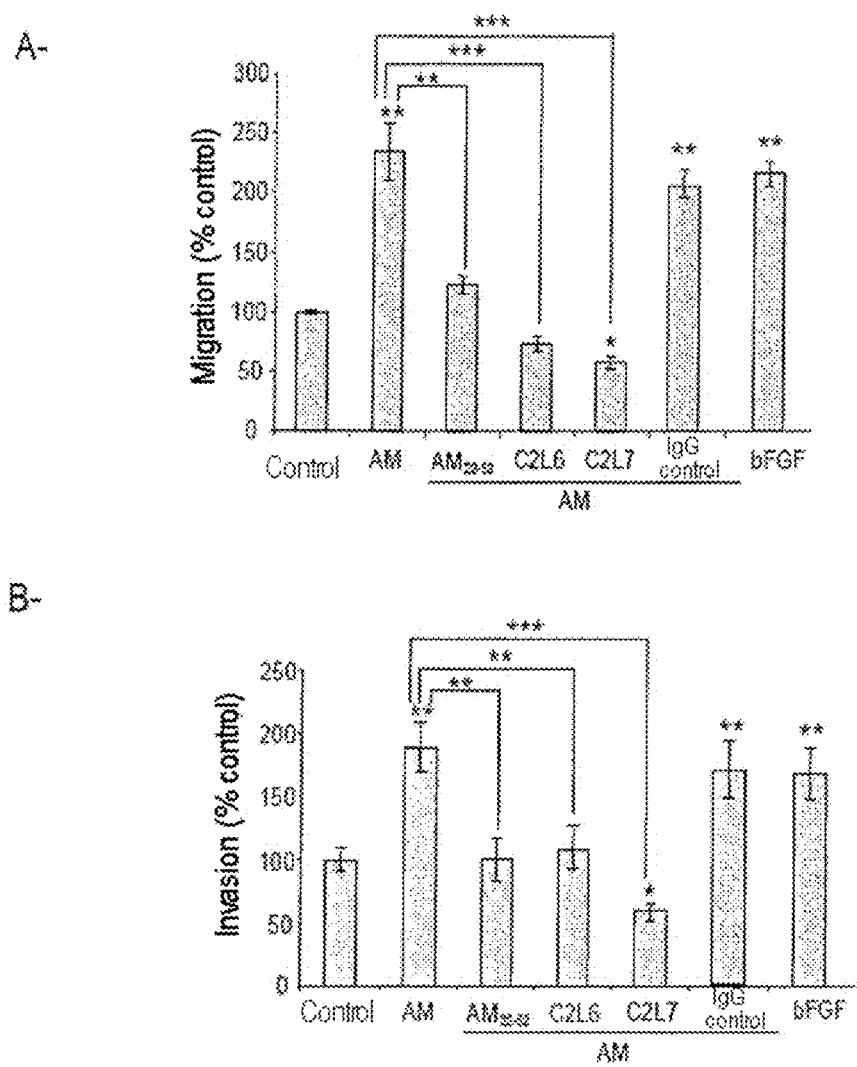

FIG. 8: inhibition of the migration and of the invasion of U87 cells by the anti-AM-CLR-RAMP3-RAMP2 chimeric polypeptide antibodies, carried out in Boyden chambers. The cells were preincubated or not preincubated with the anti-AM-CLR-RAMP3-RAMP2 chimeric polypeptide antibodies (batches C2L6 or C2L7) or with the $AM_{22-52}$ antagonist. The chemoattractants AM and bFGF were placed in the lower chamber. The controls are: cells without treatment ("Control"), cells treated with adrenomedullin (AM), cells treated with the $AM_{22-52}$ antagonist and for which AM and bFGF were placed in the lower chamber; cells treated with IgGs not specific for AM, CLR, RAMP3 and RAMP2 and for which AM and bFGF were placed in the lower chamber ("IgG Cont"); cells treated with IgGs not specific for AM, CLR, RAMP3 and RAMP2.

Figure 9:
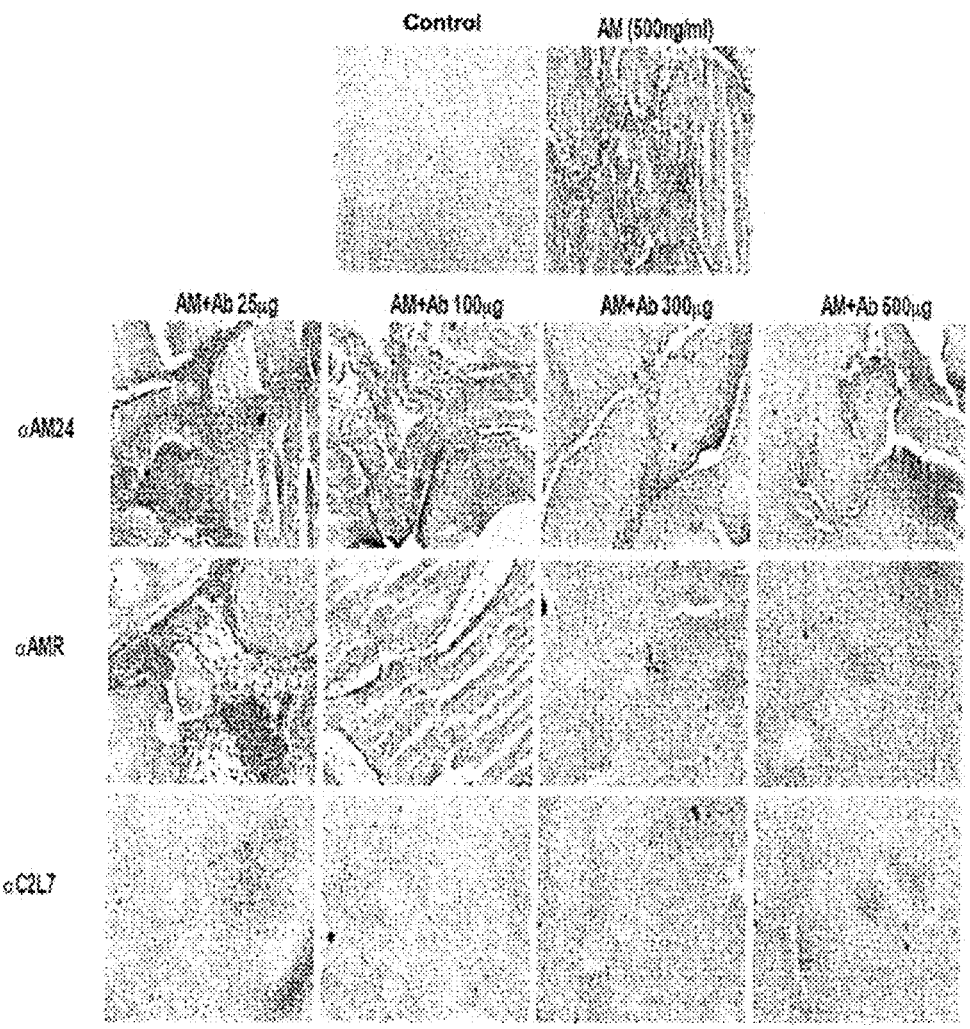

FIG. 9: Inhibition of vascular cell recruitment in an in vivo angiogenesis test. C57BL/6 mice received, by subcutaneous injection at the level of the groin, 0.5 ml of Matrigel containing AM (500 ng/ml) or not containing AM (Control). The anti-adrenomedullin ($\alpha AM_{24}$) antibodies (Ab), the anti-adrenomedullin receptor (anti-CLR, anti-RAMP2 and anti-RAMP3) ($\alpha AMR$) antibodies (Ab) or the anti-AM-CLR-RAMP3-RAMP2 chimeric polypeptide antibodies (batch C2L7) were administered at 25 µg, 100 µg, 300 µg and 500 µg/mouse intraperitoneally every 3 days. The treatments started 24 hours after the injection of the Matrigel. After 15 days of treatment, the mice were sacrificed. The Matrigels were isolated and fixed with formol, embedded in paraffin, and then sectioned (6 µm) for analysis with hematoxylin and eosin.

EXAMPLE

I. Material and Methods

I.1. Chemical Synthesis of the Chimeric Polypeptide of Sequence SEQ ID No. 10, Referred to as AM-CLR-RAMP3-RAMP2 Polypeptide (or "ch2")

The solid-phase synthesis of the polypeptide of sequence SEQ ID No. 10 was carried out according to the Merrifield method (Merrifield, Science, 1986, 232:341-347). The method is based on the use of a solid support (resin) on which the polypeptide being elongated is anchored, and on a liquid phase containing the reagents and solvents. The assembly of the polypeptide is carried out directly on the insoluble matrix contained in a reaction vessel, by incrementation of the chain from the C-terminal end to the N-terminal end, according to a series of chemical reactions corresponding to the cycle for incorporation of one amino acid. The various constituent amino acids of the peptide are therefore sequentially coupled in the polypeptide chain following this repeat cycle, as a function of the primary structure of the molecule desired. At each step of the synthesis cycle, simple filtration and washing makes it possible to remove the reagents through the filtering wall of the reaction vessel. At the end of assembly, chemical cleavage allows the "release" of the crude polypeptide into the liquid phase (Mabrouk et al., *Biochim. Biophys. Acta*, 2007, 528:2528-2540).

After purification, the peptides were characterized by mass spectrometry and by analytical high performance liquid chromatography (HPLC) (C8 reverse phase column).

I.2. Production of Anti-AM-CLR-RAMP3-RAMP2 Chimeric Polypeptide Antibodies

Immunizations

Polyclonal antibodies were obtained by injection, in rabbits, of the AM-CLR-RAMP3-RAMP2 chimeric polypeptide (antigen) (ch2; SEQ ID No. 10).

The animals were immunized with the AM-CLR-RAMP3-RAMP2 chimeric polypeptide supplemented with Freund's adjuvant. Immunization boosters were then given every 3 weeks.

Samples of the nonimmune sera (NRS), acting as a control (preimmune), were taken from the same animals before immunization.

Immunoglobulin (IgG) Purification and Endotoxin Assay

The polyclonal antibodies were purified by passing them over a gel of sepharose beads coupled to protein A (GE Healthcare) and eluted with 100 mM glycine/pH 3. The presence of endotoxin was verified using the LAL test (Limulus Amebocyte Lysate, Chambrex). The results show a tolerable level of endotoxin (<1.25 U) in the various antibody preparations and also in the preimmune serum. The immunoglobulin concentration was calculated using the Pierce method (Bicinchoninic (BCA) Protein Assays; Smith et al., *Anal Biochem*, 1985, 150:76-85).

Various batches of anti-AM, -CLR, -RAMP3 and -RAMP2 antagonist polyclonal antibodies were obtained.

I.3. Cell Culture

The U87 glioblastoma (tumor) cell lines come from the American Type Culture Collection (Rockville, Md., USA); ATCC No. HTB-14. The cells are maintained in an appropriate medium (MEM medium+2 mM glutamine+1 mM sodium pyruvate+10% FCS) in a humid atmosphere composed of 5% $CO_2$ and 95% air at 37° C.

The HT-29 colorectal cancer cell lines come from the American Type Culture Collection (Rockville, Md., USA); ATCC No. HTB-38. The cells are maintained in an appropriate medium (DMEM medium+2 mM glutamine+10% fetal bovine serum (FBS)).

The media are renewed every two days. When the cells reached 90% confluence, they were detached with a solution of trypsin (0.25%) in Tris buffer (Gibco) for a few minutes at 37° C. The action of the enzyme was stopped by adding medium containing serum. The cells were seeded either into 75 $cm^3$ tubes or into multiwell plates in their appropriate media.

I.4. Demonstration of the Specificity of Binding of the Anti-AM-CLR-RAMP3-RAMP2 Chimeric Polypeptide Antibodies a) 750 ng of adrenomedullin (AM), 750 ng of hRAMP3 protein, 500 ng of hCLR protein, 500 ng of hRAMP2 protein and 20 ng of AM-CLR-RAMP3-RAMP2 chimeric polypeptide were separated by SDS-PAGE on a 17% acrylamide gel, and then visualized with the anti-AM-CLR-RAMP3-RAMP2 chimeric polypeptide antibodies or with the non-reactive serum (NRS), used at 1/250.

b) 20 µg of protein extracts prepared from U87 glial tumor cells were separated by SDS-PAGE on a 12% acrylamide gel, and then visualized with the anti-AM-CLR-RAMP3-RAMP2 chimeric polypeptide antibodies or with the non-reactive serum (NRS), used at 1/250.

I.5. In Vitro Studies

In Vitro Study of the Effect of the Anti-AMP-CLR-RAMP3-RAMP2 Chimeric Polypeptide Polyclonal Antibodies on the Growth of U87 Glial Tumor Cells and of HT-29 Colorectal Cancer Cells The U87 glial tumor or HT-29 colorectal cancer cells were respectively seeded into 24-well plates (2000 cells/well) in DMEM medium in the presence of 2% of serum (2% of bovine fetal serum in 100 ml of culture medium) and then treated for 6 days with the anti-AM-CLR-RAMP3-RAMP2 chimeric polypeptide polyclonal antibodies or with the non-reactive serum (NRS) in 2%-serum medium. An MTT test (Ouafik et al., Am J Pathol., 2002, 160:1279-92; Kaafarani et al., FASEB J., 2009, 23:3424-35) was then used to evaluate the amount of cells at the end of the treatment.

In Vitro Studies of the Effect of the Anti-AM-CLR-RAMP3-RAMP2 Chimeric Polypeptide Polyclonal Antibodies on the Migration of U87 Glial Tumor Cells $1^{st}$ study: 20 000 U87 glial tumor cells were seeded into Boyden chambers in 2%-serum medium after having been pretreated or not (contAM) with the anti-AM-CLR-RAMP3-RAMP2 chimeric polypeptide polyclonal antibodies or with the nonreactive serum (NRS), and were then subjected for 4 h to the chemoattractive effect of adrenomedullin ($10^{-7}$ M) located in the lower compartment of the Boyden chamber. A negative control was performed by omitting the adrenomedullin in the lower compartment of the Boyden chamber (cont-). The evaluation of the number of cells having migrated was carried out by counting under a microscope after Dapi (4',6'-diamidino-2-phenylindole) staining.

$2^{nd}$ study: The migration and invasion tests were carried out in Boyden chambers, with polycarbonate filters having pores 8 µm in diameter. The filters of the wells were incubated for 1 h at 37° C. with a solution of fibronectin (10 µg/ml, Sigma Aldrich) diluted in PBS for the migration and with a solution of matrigel at 0.05 mg/ml for the invasion.

10 000 U87 cells were deposited per well in DMEM-2 mM L-glutamine-2% FBS medium. The cells were preincubated or not preincubated with the anti-AM-CLR-RAMP3-RAMP2 chimeric polypeptide antibodies (batches C2L6 or C2L7) (70 µl/ml) or with the $AM_{22-52}$ antagonist ($10^{-6}$ M) (Ouafik et al., Am J Pathol., 2002, 160:1279-92) for 30 min at 37° C.

The chemoattractants, AM ($10^{-7}$ M), bFGF ($10^{-6}$ M), were placed in the lower chamber. The plates were then placed at 37° C. in a humid atmosphere containing 5% $CO_2$ for 2 h. Fixing with paraformaldehyde (4% PAF) was carried out for 30 minutes at 37° C. The upper face of the filter, containing the cells which have not migrated, was carefully cleaned with a cotton wool bud after having been washed with PBS. On the lower face, the cells having migrated were stained with DAPI (Invitrogen Life Technologies) and the number of nuclei was quantified using the Image J1.43u image analysis software. The values representing the mean±SEM ("Standard Error of the Mean") of 3 independent experiments each were produced in triplicate (p<0.01; *p<0.001).

I.6. Western Blotting Analyses

Protein Extract Preparation

The cell pellets originating from U87 glial tumor cells or the homogenates obtained from glial tumors xenografted into nude mice were taken up in a lysis buffer (20 mM HEPES, pH 7.9, 10 mM NaCl, 1 mM $MgCl_2$, 10% glycerol, 0.2 mM EDTA, 0.5 mM DTT, 1% protease inhibitors and 0.35% of Triton X-100) and homogenized at 4° C. After centrifugation at 12 000×g for 10 minutes, the supernatant containing the proteins was recovered and the proteins were quantified by the Pierce method.

Western Blotting

The cell lysates (50 µg) were separated by electrophoresis on a 12% polyacrylamide gel under denaturing and reducing conditions. At the end of the migration in a 0.25 M Tris-base buffer containing 1.92 M glycine and 1% SDS, the proteins were transferred onto a polyvinylidene fluoride (PVDF) membrane at 1 $mA/cm^2$ for 1 h 30. The membranes were saturated for 1 h at ambient temperature in PBS-5% skimmed milk. After 2 washes (PBS 0.2%-Tween 20), the membranes were incubated with agitation overnight at 4° C. in the presence of the anti-AM-CLR-RAMP3-RAMP2 chimeric polypeptide antibodies diluted to 1/400 in PBS-1% skimmed milk. After 3 washes (PBS 0.2%-Tween 20), the membranes were incubated for 1 h 30 at ambient temperature with the peroxidase-labeled secondary antibody (ECL kit, GE Healthcare, Amersham). The signal was visualized using the chemoluminescence kit (ECL kit, GE Healthcare, Amersham).

20 µg of protein extracts prepared from U87 glial tumor cells were separated by SDS-PAGE on a 12% polyacrylamide gel, and then visualized with the anti-AM-CLR-RAMP3-RAMP2 chimeric polypeptide polyclonal antibodies used at 1/250 or at 1/10 000, or used at 1/50 000 and preincubated for 30 min with 0.7 µg/ml of adrenomedullin (AM), hCLR, hRAMP2 or hRAMP3 or 1.4 µg/ml of hCLR/hRAMP2, hCLR/hRAMP3 or hRAMP2/hRAMP3 protein complexes or 2.1 µg/ml of hCLR/hRAMP2/hRAMP3 protein complex or 0.7 µg/ml of AM-CLR-RAMP3-RAMP2 chimeric polypeptide.

I.7. In Vivo Studies
Animal Models

Athymic (nu/nu) female Balb/C mice and C57BL/6 mice (Harlan, France) 4-5 weeks old were used. They were kept under sterile conditions, at a stable temperature and received and appropriate diet. The in vivo experiments start only after a period of adaptation of the animals to their new environment (10-15 days after reception).

Xenograft Development and Animal Treatments

Cells of the U87 tumor line were injected subcutaneously into the flank of athymic (nu/nu) mice in a proportion of $2.5 \times 10^6$ cells per animal. The animals were weighed regularly and the tumor volume was measured 3 times a week and calculated according to the ellipsoid formula V=Length×width×thickness×0.5236 mm³.

When the tumors reached a tumor volume of 500-1000 mm³ (12-15 days after injection of the cells), the animals were treated intratumorally or intraperitoneally with the anti-AM-CLR-RAMP3-RAMP2 chimeric polypeptide antibodies (see section I.2 above), the final concentration of which was 350 µg/animal, this being at a rate of 3 injections/week. The groups of animals acting as a control were treated in the same way, but with a preimmune serum (NRS). The tumor volumes were measured three times a week. The values are the mean±SE (standard error) of 5 mice/group.

Animals were sacrificed at varying times during the treatment (d2, d7, d11, d16 and d21). The tumors were immediately removed and fixed in formol. They were then embedded in paraffin for the immunohistochemical studies.

One group of animals treated for 21 days received an injection of biotinylated lectin (Biotinylated-Lycopersicon esculentum (tomato) lectin, CliniSciences) under anesthesia. The animals were perfused with a 4% paraformaldehyde solution which makes it possible to fix the tissues in vivo. The tumors and several organs (brain, lung, heart and kidney) were removed and frozen in liquid nitrogen for histology and immunohisto-chemistry studies.

Inhibition of Vascular Cell Recruitment in an In Vivo Angiogenesis Test

C57BL/6 mice received, by subcutaneous injection at the level of the groin, 0.5 ml of matrigel containing AM (500 ng/ml) or not containing AM (Control). The anti-adrenomedullin ($\alpha AM_{24}$) antibodies, the anti-adrenomedullin receptor (anti-CLR, anti-RAMP2 and anti-RAMP3) ($\alpha AMR$) antibodies or the anti-AM-CLR-RAMP3-RAMP2 chimeric polypeptide antibodies (batch C2L7) were administered at 25 µg, 100 µg, 300 µg and 500 µg/mouse (n=4) intraperitoneally every 3 days. The treatments started 24 hours after the injection of the matrigel. After 15 days of treatment, the mice were sacrificed. The matrigels were isolated and fixed with formol, embedded in paraffin, and then sectioned (6 µm) for the analysis with hematoxylin and eosin.

Immunofluorescence Analyses a) The tumors of mice treated with 350 µg/animal of anti-AM-CLR-RAMP3-RAMP2 chimeric polypeptide antibodies were removed, fixed, and embedded in paraffin. Sections 6 µm thick were cut on a microtome. After deparaffinization and rehydration, the slides were subjected to epitope unmasking by heating at 95° C. in a Tris-EDTA buffer (pH 9). After treatment, the sections were incubated overnight at 4° C. with the anti-vWF antibody (1/400; Dako), specific for endothelial cells. The following day, the slides were washed and then incubated with the peroxidase secondary antibody. The presence of the antibody is then demonstrated by DAB staining. The analysis of the labeling was carried out with a Leica microscope equipped with a fluorescence lamp.

b) The control matrigels, the matrigels treated with AM and those where the mice were treated with 25 µg of anti-AM-CLR-RAMP3-RAMP2 chimeric polypeptide antibody were analyzed by immunofluorescence in order to evaluate the neoangiogenesis. For this purpose, after rehydration of the matrigel, colabeling with the anti-factor VIII antibody (vWF; endothelial cell-specific marker) and the anti-α-SMA antibody (marker specific for wall cells, the pericytes) was carried out. The sections were incubated overnight at 4° C. with the anti-α-SMA (1/80; Dako) and anti-vWF (1/100; Dako) antibodies. The following day, the slides were washed and then incubated with the antibodies coupled to a fluorochrome (Alexa 488 or Alexa 568) for 2 hours at ambient temperature in the dark and then with DAPI (nuclear marker; 1/20 000 of a solution at 2 mg/ml) (Invitrogen Life Technologies). The slides were mounted and the analysis was carried out using a Leica microscope equipped with a fluorescence lamp.

II. Results

II.1. Demonstration of the Specificity of the Anti-AM-CLR-RAMP3-RAMP2 Chimeric Polypeptide Antibodies The results of the Western blotting are represented in FIG. 1. These results show that the anti-AM-CLR-RAMP3-RAMP2 chimeric polypeptide polyclonal antibodies (referred to as ch2) bind to adrenomedullin (AM), hCLR (CLR), hRAMP2 (R2) and hRAMP3 (R3), and also to the hCLR/hRAMP2, hCLR/hRAMP3, hRAMP2/hRAMP3 and hCLR/hRAMP2/hRAMP3 complexes, whereas the nonreactive sera (NRS) do not bind to these proteins or protein complexes (see FIGS. 1A and 1B).

II.2. In Vitro Antitumor Efficacy

The analysis by the Western blotting technique shows that the anti-AM-CLR-RAMP3-RAMP2 chimeric polypeptide antibodies are capable of recognizing the AM, RAMP2 and CLR peptides. Very advantageously, they recognize the complexes formed by the interaction CLR/RAMP2 and CLR/RAMP3 which have a molecular weight of 73 kDa. These antibodies are capable of recognizing the CLR protein of 48 kDa, the RAMP2 or RAMP3 homodimers having a size of 50-52 kDa, two glycosylated monomeric RAMP2 forms having respectively a size of 22 or 31 kDa and a glycosylated monomeric RAMP3 form having a size of 27 kDa (see FIGS. 1C and 3).

The incubation of the U87 glial tumor cells with the anti-AM-CLR-RAMP3-RAMP2 chimeric polypeptide antibodies demonstrates an inhibition of the proliferation of these cells in a dose-dependent manner (see FIGS. 2 and 4). These inhibition experiments thus demonstrate the presence of an autocrine and/or paracrine loop involving adrenomedullin and its CLR, RAMP2 and RAMP3 receptors in the proliferation of the tumor cells.

Figure 5:
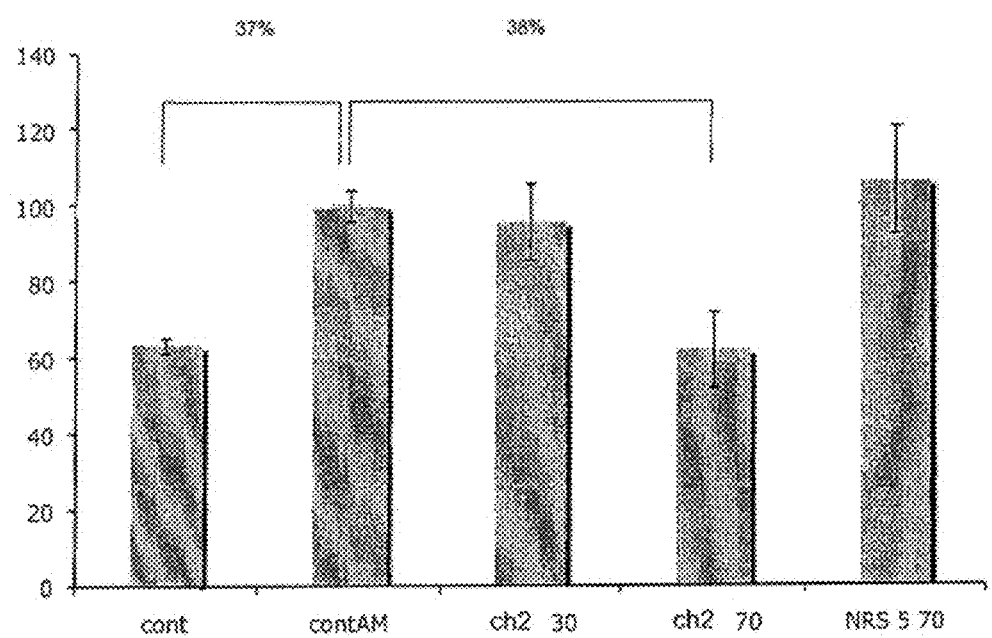

Furthermore, these anti-AM-CLR-RAMP3-RAMP2 chimeric polypeptide antibodies have an ability to inhibit the AM-induced migration of U87 cells in a dose-dependent manner ($1^{st}$ migration study, see FIG. 5). However, no inhibition effect was observed on the cells preincubated with the NRS (see FIG. 5).

II.3. Inhibition of the Proliferation of U87 Glioblastoma Cells and of HT-29 Colorectal Cancer Cells by anti-AM-CLR-RAMP3-RAMP2 Chimeric Polypeptide Antibodies The results are represented in FIG. 7. The incubation of the U87 cells (A) and of the HT-29 cells (B) with two different batches of anti-AM-CLR-RAMP3-RAMP2 chimeric polypeptide polyclonal antibodies (batches C2L6 and C2L7) for 6 days caused inhibition of proliferation. This decrease reaches 73±4.5% for the U87 cells and 42.9±1.1% for the HT-29 cells, relative to the control cells and to the cells treated with exogenous adrenomedullin (AM; SEQ ID No. 1) at $10^{-7}$ M. Treatment with the $AM_{22-52}$ antagonist at $10^{-6}$ M was used as a positive control for inhibition of proliferation.

These results demonstrate that the anti-AM-CLR-RAMP3-RAMP2 chimeric polypeptide antibodies inhibit the autocrine/paracrine loop involving AM and its receptors (CLR/RAMP2; CLR/RAMP3) in the growth of tumor cells in vitro.

II.4. Inhibition of the Migration and the Invasion of U87 Cells by the Anti-AM-CLR-RAMP3-RAMP2 Chimeric Polypeptide Antibodies ($2^{nd}$ Migration Study)

The results are represented in FIG. 8. These results show the ability of the anti-AM-CLR-RAMP3-RAMP2 chimeric polypeptide antibodies to inhibit the migration and the invasion of U87 cells. It should be noted that batch C2L7 is capable of significantly inhibiting the migration and the invasion stimulated by the endocrine action of AM on its receptors, relative to the controls.

II.5. In Vivo Antitumor Efficacy

The tumors developed in the athymic mice after subcutaneous injection of cells of the U87 cell line represent an experimental model which takes into account all the components of the tumor microenvironment.

Intraperitoneal Administration of the Antibodies

The intraperitoneal administration of the anti-AM-CLR-RAMP3-RAMP2 chimeric polypeptide antibodies induces an inhibition of xenograft tumor growth of 50% to 70% after 20 days of treatment (see FIG. 6). After 16 days of treatment, it was observed that the tumors of animals treated with the anti-AM-CLR-RAMP3-RAMP2 chimeric polypeptide antibodies appeared pale, translucent and less vascularized. Conversely, the control animals exhibited highly vascularized large tumors. These important effects observed in vivo imply that, in addition to an action on tumor cell proliferation, the treatment with the anti-AM-CLR-RAMP3-RAMP2 chimeric polypeptide antibodies disrupts a fundamental mechanism essential to tumor growth.

Immunofluorescence Analyses

The results clearly show a destabilization of the intratumor vascularization in the group of animals treated with the anti-AM-CLR-RAMP3-RAMP2 chimeric polypeptide antibodies compared with the group treated with the control IgGs.

II.6. Inhibition of Vascular Cell Recruitment in the In Vivo Angiogenesis Test

The results are represented in FIG. 9. They clearly show the ability of the anti-AM-CLR-RAMP3-RAMP2 chimeric polypeptide antibodies to inhibit cell recruitment from the first dose used, of 25 µg/mouse. The equivalent of this inhibition for the αAMRs is observed only with doses of 300 µg/mouse, whereas, with $\alpha AM_{24}$, the inhibition remains partial even at doses of 500 µg/mouse.

These results demonstrate the advantage and the value of using the anti-AM-CLR-RAMP3-RAMP2 chimeric polypeptide antibodies for drastically inhibiting the effect of AM and its receptors, compared with an anti-adrenomedullin antibody or with a mixture of 3 anti-adrenomedullin receptor antibodies (anti-CLR, anti-RAMP2 and anti-RAMP3).

Immunofluorescence Analyses

The results show a stable vascularization which has been set up in the matrigel containing the AM and which persists in the mice treated with 25 µg of $\alpha AM_{24}$ and αAMR antibodies. Unexpectedly, the complete disappearance of this vascularization is observed during the treatment with 25 µg of anti-AM-CLR-RAMP3-RAMP2 chimeric polypeptide antibodies. A few endothelial cells are therefore observed without the presence of pericytes.

These results strongly suggest the ability of the anti-AM-CLR-RAMP3-RAMP2 chimeric polypeptide antibodies to inhibit the recruitment and the maintaining of vascular cells (endothelial cells and pericytes) in the in vivo angiogenesis test. The control matrigel shows a few cells detected by virtue of DAPI and which are neither endothelial nor pericytic in nature.

The invention claimed is:

1. A composition comprising a mixture of at least 4 antibodies and/or fragments of said antibodies, wherein:
    said antibodies and/or antibody fragments bind to four proteins selected from the group consisting of adrenomedullin, calcitonin receptor like receptor (CLR), receptor activity-modifying protein 2 (RAMP2) and receptor activity-modifying protein 3 (RAMP3)
    each of said antibodies and/or antibody fragments bind to a different protein,
    said antibodies and/or antibody fragments are antagonists of adrenomedullin, CLR, RAMP2 and RAMP3,
    one of the at least four antibodies and/or antibody fragments binds to an extracellular domain of CLR and is obtained by immunization of an animal with a peptide sequence selected from the group consisting of SEQ ID No. 3 and SEQ ID No. 4,
    one of the at least four antibodies and/or antibody fragments binds to an extracellular domain of RAMP2 and is obtained by immunization of an animal with a peptide sequence selected from the group consisting of SEQ ID No. 5 and SEQ ID No. 6, and/or
    one of the at least four antibodies and/or antibody fragments binds to an extracellular domain of RAMP3 and is obtained by immunization of an animal with a peptide sequence selected from the group consisting of SEQ ID No. 7, SEQ ID No. 8 and SEQ ID No. 9.

2. The composition as claimed in claim 1, wherein the composition contains the antibodies and/or antibody fragments in an amount effective to inhibit angiogenesis upon administration to a subject.

3. The composition as claimed in claim 2, wherein the composition contains an amount of antibody and/or antibody fragments sufficient for the treatment of a disease in which angiogenesis must be inhibited.

4. The composition as claimed in claim 1, wherein the adrenomedullin and the CLR, RAMP2 and RAMP3 proteins are of human origin.

5. The composition as claimed in claim 1, wherein said antibodies are polyclonal and/or monoclonal antibodies.

6. A method of producing the composition of claim 1, comprising immunizing an animal with a chimeric polypeptide comprising four immunogenic peptide fragments of at least 6 contiguous amino acids from adrenomeddulin and from an extracellular domain of the CLR, RAMP2 and RAMP3 proteins, wherein the peptide fragment from adrenomedullin has the sequence SEQ ID No. 2, the peptide fragment from the CLR protein has the sequence SEQ ID No. 3 or SEQ ID No. 4, the peptide fragment from the RAMP2 protein has the sequence SEQ ID No. 5 or SEQ ID No. 6, and the peptide fragment from the RAMP3 protein has the sequence SEQ ID No. 7, SEQ ID No. 8 or SEQ ID No. 9, wherein said chimeric polypeptide induces, in said animal immunized with said chimeric polypeptide, the production of polyclonal antibodies which bind to adrenomedullin, CLR, RAMP2 and RAMP3.

7. The method of claim 6, wherein the chimeric polypeptide has the sequence of SEQ ID No. 10.

8. A pharmaceutical composition, which comprises at least one mixture of antibodies and/or antibody fragments, as defined in claim 1, and at least one pharmaceutically acceptable vehicle.

9. The method of claim 6, wherein the chimeric polypeptide is present in an amount sufficient to produce an immunogenic response against adrenomedullin, CLR, RAMP2 and/or RAMP3 when administered to a subject.

10. The method of claim 9, wherein the chimeric polypeptide is in a composition, and the composition is a vaccine for the treatment of a disease in which angiogenesis must be inhibited.

11. The composition as claimed in claim 1, wherein said antibodies and/or antibody fragments are obtained by immunizing an animal with a chimeric polypeptide comprising four immunogenic peptide fragments of at least 6 contiguous amino acids, respectively, from adrenomedullin and from an extracellular domain of the CLR, RAMP2 and RAMP3proteins, and the peptide fragment from adrenomedullin has the sequence SEQ ID No. 2, the peptide fragment from the CLR protein has the sequence SEQ ID No. 3 or SEQ ID No. 4, the peptide fragment from the RAMP2 protein has the sequence SEQ ID No. 5or SEQ ID No. 6, and the peptide fragment from the RAMP3 protein has the sequence SEQ ID No. 7, SEQ ID No. 8 or SEQ ID No. 9, wherein said chimeric polypeptide induces, in said animal immunized with said chimeric polypeptide, the production of polyclonal antibodies which bind to adrenomedullin, CLR, RAMP2 and RAMP3.

12. The composition as claimed in claim 1, wherein the chimeric polypeptide has the sequence SEQ ID No. 10.

13. An immunogenic composition, which comprises a chimeric polypeptide comprising four immunogenic peptide fragments of at least 6 contiguous amino acids, respectively, from adrenomedullin and from an extracellular domain of the CLR, RAMP2 and RAMP3proteins, wherein the peptide fragment from adrenomedullin has the sequence SEQ ID No. 2, the peptide fragment from the CLR protein has the sequence SEQ ID No. 3 or SEQ ID No. 4, the peptide fragment from the RAMP2 protein has the sequence SEQ ID No. 5 or SEQ ID No. 6, and the peptide fragment from the RAMP3 protein has the sequence SEQ ID No. 7, SEQ ID No. 8 or SEQ ID No. 9, wherein said chimeric polypeptide induces, in said animal immunized with said chimeric polypeptide, the production of polyclonal antibodies which bind to adrenomedullin, CLR, RAMP2 and RAMP3, combined with at least one pharmaceutically acceptable vehicle.

14. The immunogenic composition as claimed in claim 13, wherein the chimeric polypeptide has the sequence SEQ ID No. 10.

15. A method of obtaining polyclonal antibodies which bind to adrenomedullin or to the CLR, RAMP2 or RAMP3 proteins, comprising a step of immunizing an animal with a chimeric polypeptide comprising four immunogenic peptide fragments of at least 6contiguous amino acids, wherein the peptide fragment from adrenomedullin has the sequence SEQ ID No. 2, the peptide fragment from the CLR protein has the sequence SEQ ID No. 3 or SEQ ID No. 4, the peptide fragment from the RAMP2 protein has the sequence SEQ ID No. 5 or SEQ ID No. 6, and the peptide fragment from the RAMP3protein has the sequence SEQ ID No. 7, SEQ ID No. 8 or SEQ ID No. 9, in an amount sufficient to produce an immungenic response in the animal.

16. The method of claim 15, wherein the chimeric polypeptide has the sequence SEQ ID No. 10.

* * * * *